(12) United States Patent
Klein et al.

(10) Patent No.: US 6,605,444 B1
(45) Date of Patent: Aug. 12, 2003

(54) METHOD AND DEVICE FOR OBTAINING AND DETECTING IMMUNOLOGICALLY ACTIVE SUBSTANCES FROM THE GAS PHASE

(75) Inventors: Christian Klein, Weilheim (DE); Hans-Peter Josel, Weilheim (DE); Rupert Herrmann, Weilheim (DE); Josef Maier, Weilheim (DE); Harald Ertl, Gelting (DE); Helmut Oberpriller, Westerhamm (DE); Reinhold Hilpert, Moorenweis (DE); Florian Binder, Traunstein (DE); Josef Ritter, Munich (DE)

(73) Assignees: Securetec Detektions-Systems AG, Ottobrunn (DE); Deutsche Aerospace AG, Munich (DE)

( * ) Notice: Subject to any disclaimer, the term of this patent is extended or adjusted under 35 U.S.C. 154(b) by 1190 days.

(21) Appl. No.: 08/898,085

(22) Filed: Jul. 22, 1997

Related U.S. Application Data

(63) Continuation-in-part of application No. 08/325,516, filed on Oct. 19, 1994, now abandoned.

(30) Foreign Application Priority Data

Oct. 20, 1993 (DE) .......................................... 43 35 780
Jul. 22, 1994 (DE) .......................................... 44 25 963

(51) Int. Cl.[7] .............................................. G01N 33/53
(52) U.S. Cl. ........................... 435/7.9; 422/58; 422/60; 422/68.1; 422/82.04; 422/83; 435/7.1; 435/7.92; 435/7.93; 435/7.94; 435/7.95; 435/287.7; 435/970; 435/971; 436/518; 436/530; 436/807
(58) Field of Search ...................... 422/58, 60, 68.1, 422/82.04, 83; 435/7.1, 7.92, 7.93, 7.94, 7.95, 287.7, 970, 971; 436/518, 530, 807

(56) References Cited

U.S. PATENT DOCUMENTS 4,806,312 A * 2/1989 Greenquist .................... 422/56
5,219,528 A * 6/1993 Clark .......................... 422/101
5,328,823 A * 7/1994 Spencer ......................... 435/4

FOREIGN PATENT DOCUMENTS

CA        2141082    *  1/1995
DE     41 21 493 A1     1/1993

(List continued on next page.)

OTHER PUBLICATIONS

Hilpert et al Cargo Inspection Technologies, 1994, 128–138 vol. 2276.*

(List continued on next page.)

*Primary Examiner*—Bao-Thuy L. Nguyen
(74) *Attorney, Agent, or Firm*—Rothwell, Figg, Ernst & Manbeck

(57) ABSTRACT

A method is disclosed for obtaining and/or immunologically detecting an analyte contained in a gas phase by immunologically binding the analyte to a binding partner thereof contained in a gas- and liquid-permeable first carrier matrix. Said method is characterized in that
  a) the analyte-containing gas phase is brought into contact with the first carrier matrix (immune adsorber),
  b) the analyte is bound to the first binding partner which is contained in the first matrix and not bound to the matrix, and
  c) the complex of analyte and first binding partner and the free first binding partner are eluted from the first matrix,
  d) the eluted complex or the free first binding partner is determined as a measure for the amount of analyte present.

6 Claims, 5 Drawing Sheets

FOREIGN PATENT DOCUMENTS

| | | |
|---|---|---|
| EP | 0 139 373 | 5/1985 |
| WO | WO93/11430 | 6/1993 |

OTHER PUBLICATIONS

Ijselmuiden et al Journal of Immunological Methods vol. 119, 35–43, 1989.*

Journal of the American Chemical Society, vol. 108, Oct. 1986 pp. 5444–5447, "Parathion antibodies on piezoelectric crystals".

WO–A–87 07724 published Dec. 17, 1987.

* cited by examiner

METHOD AND DEVICE FOR OBTAINING AND DETECTING IMMUNOLOGICALLY ACTIVE SUBSTANCES FROM THE GAS PHASE

This application is a continuation of application Ser. No. 08/325,516 filed Oct. 19, 1994, now abandoned.

Subject matter of the invention is a method and device for obtaining and detecting immunologically active substances (e.g. drugs of abuse) from the gas phase by means of an immunological procedure.

The detection of immunologically active substances from the gas phase has gained particular importance for the detection of drugs of abuse, such as cocaine and cannabinoids.

To date, various techniques and technologies (X-ray instruments, GC-MS coupling, GC with chemiluminescence detectors) are used to carry out stationary tests for the presence of illegal drugs of abuse, e.g. in baggage. However, size and weight of these systems and the high costs involved contradict the common use of these techniques. Principally, all portable instruments whose function is based on ion mobility spectroscopy (IMS) are suitable for use anywhere. They involve, however, problems with respect to selectivity and sensitivity. Moreover, these instruments are only suitable to detect contamination which is present in the form of particles. The only method for the selective detection of narcotics in the gas phase is currently the use of drug-sniffing dogs. The disadvantage involved with the use of such animals is, however, the short time for which the animals are available, the fact that they can be distracted, the presence of irritating substances, and the high costs. A portable instrument for the selective detection of narcotics which can be used under various conditions would, hence, constitute an enormous progress in the fight against illegal drug trafficking.

Biosensors making use of the principle of an immunological reaction between the analyte and binding partners contained in the biosensor would be potentially suitable for such tasks due to the high selectivity and specificity of the immunological reactions. A biosensor of this kind has been described by Ngen-Ngwainbi, J., et al. in J. Am. Chem. Soc. 108 (1986), 5444–5447. In this literature reference, an antibody to a cocaine metabolite (benzoylecgonine) as a reactive component of the sensor is used as a Piezo transducer with a resonance frequency of 9 MHz. The antibody is immobilized through physical adsorption on the surface of the sensor. The lower detection limit is at 0.5 ppb corresponding to $2 \times 10^{-11}$ mol/l in gas phase (for cocaine and cocaine-HCl). As the mass sensitivity of the transducer is very low, the performance of such an instrument is not suitable for use in the practice.

Another method is described in JP-A-0374460. In this literature reference, drug molecules from the gas phase are adsorbed to a polyethersulfone membrane, then eluated and detected in the eluate in an immunological reaction. Again, the sensitivity is very low.

Another method is described in DE-A 41 21 493. According to this reference, immobilized antibodies and labeled tracers (which correspond to the analyte) are bound to one another and present in a permeable, non-transparent partial area of the carrier. The analyte is added and replaces labeled tracers prior to binding to the antibody. The free labeled tracer diffuses then into a transparent part of the carrier. The progress of the tracer diffusion can be monitored as it causes a discoloration, since the label used in the tracer is a dye. Again, this is a method which exhibits a very low sensitivity.

The detection limits necessary for a successful detection of drugs of abuse from the gas phase cannot be reached with these methods.

Cocaine, for example, has a saturation concentration of $6 \times 10^{-12}$ mol/l gas phase at 20° C. In the practice, however, concentrations are considerably lower so that the lower detection limit of a method necessary for successful detection ranges between $10^{-13}$ to $10^{-15}$ mol/l gas phase.

As it is not possible to measure such low concentrations directly from the gas phase, a device for determining immunologically active substances from the gas phase advantageously comprises an adsorption unit and a detection unit.

In the fight against drugs, it is also necessary to detect particle-like drugs or drugs that are bound to particles in addition to drug molecules which occur freely in the gas phase (edited by BKA, "Internationales Symposium Detektion von Rauschgift", Wiesbaden 1991).

It is an object of the present invention to provide a method of obtaining immunologically active substances from the gas phase which can be used to convert the substance to be detected from the gas phase into a form suitable for subsequent detection reactions.

Another object of the invention is the provision of a method of determining immunologically active substances from the gas phase which exhibits a high sensitivity and allows quick adsorption or adsorption and determination.

Immunologically active substances from the gas phase are substances which occur freely in the gas phase, particles of these substances or substances bound to particles which can be obtained from the gas phase.

Figure 1A:
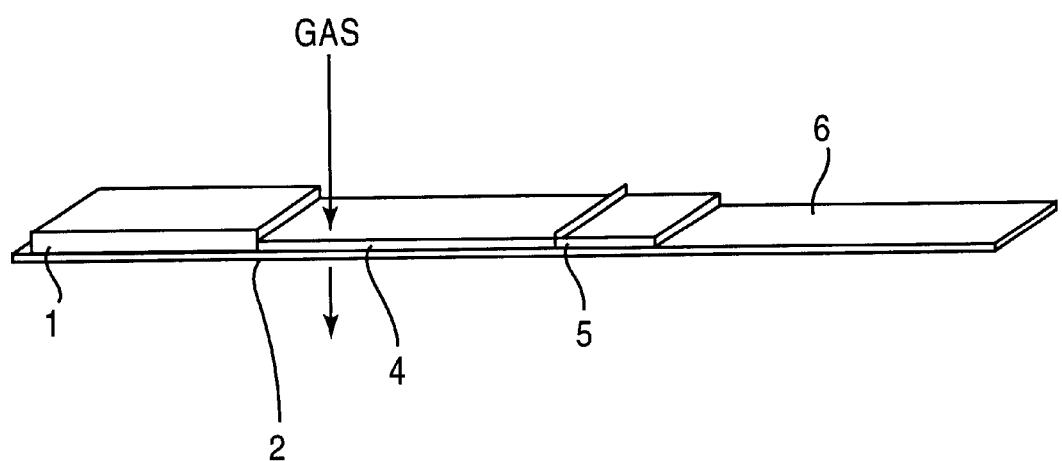
FIGS. 1a and 1b show different views of a test carrier containing a fleece for receiving elution liquid, an immune-absorbing matrix above an adsorption opening of the carrier foil, an adsorption opening, a capture matrix and a detection matrix.

Subject matter of the invention is a method of obtaining an analyte contained in a gas phase by immunologically binding this analyte to a binding partner of said analyte contained in a gas- and liquid-permeable first matrix. The method is characterized in that a) the analyte-containing gas phase is brought into contact with the first carrier matrix (immune adsorber), b) the analyte is bound to the first binding partner which is contained in the first matrix and not bound to the matrix, and c) the complex consisting of analyte and first binding partner and uncomplexed first binding partner are eluted from the first matrix, and d) optionally the analyte is released from the complex.

Another subject matter of the invention is a method of immunologically detecting an analyte contained in the gas phase by immunologically binding the analyte to a binding partner of said analyte contained in a gas- and liquid-permeable first carrier matrix. This method is characterized, in that a) the analyte-containing gas phases brought into contact with the first carrier matrix (immune adsorber), b) the analyte is bound to the first binding partner which is contained in the first matrix and not bound to the matrix, and c) the mixture consisting of complex of analyte and first binding partner and free (uncomplexed) first binding partner is eluted from the first matrix and d) the eluted complex or the free first binding partner are determined as a measure for the amount of analyte present.

Suitable binding partner of the analyte are antibodies which may be monoclonal or polyclonal antibodies, or fragments (e.g. Fab, Fab') thereof. Also suitable are receptors which are present in the body, as these bind drugs, e.g. a cannabinoid receptor (Matsuda et al., Nature 346 (1990) 561–564).

Preferred carrier matrices consist of hydrophilic or hygroscopic materials, e.g. based on cellulose, modified cellulose such as cellulose nitrate or cellulose acetate, hydroxyalkylated cellulose, or modified and unmodified cellulose crosslinked with substances such as epichlorhydrin. Also suitable are glass fiber matrices and matrices consisting of polyester. These materials can either be used solely or in combination with other compound materials with a hydrophilic portion in the carrier matrix prevailing.

In a preferred manner, the first carrier materials and, optionally, other carrier materials are structured so as to form particles (e.g. pearl-like, see DD-A 296 005) or fibers, such as filter papers on cellulose basis (EP-A 374 684, EP-A 0 470 565). Other materials used for the construction of the test carriers are described in EP-A 0 374 684, EP-A 0 353 570 and EP-A 353 501.

The first carrier matrix must be gas-permeable to allow enrichment of the immunologically active substance from the gas phase. For pressure gradients above the adsorber (200–500 mbar) which are technically easy to implement, the gas permeabilities advantageously range between 1 ml/min and 100 l/min, preferably between 100 ml/min and 20 l/min and particularly preferred between 500 ml/min and 10 l/min.

In addition to keeping back the analyte, another essential requirement of first matrix (immune adsorber) is to allow the immune reaction to occur between the binding partner and the immunologically active substance, e.g. via diffusion. To accomplish this, the first matrix can contain the necessary liquids either before the beginning of the adsorption or the first matrix can be essentially dry and the immune reaction can be allowed to occur after adding liquid. An essentially dry matrix as used in the presently claimed invention, is a matrix in which there is no measurable amount of liquid.

The preferred liquid in the first matrix is water. If the first matrix contains liquid already before the adsorption, the contents thereof ranges between 10 and 90% of the total weight of the first matrix. The water used can have a percentage of up to 30 wt. % of organic substances as a dissolving agent (e.g. dimethylsulfoxide, glycerol).

In order to increase the solubility of the binding partners, it is preferred to add 0.01 to 1% of detergents (e.g. Tween 20™, Tween 80™, octylglucoside, polydocanol and/or Synperonic™, e.g. F 68).

If the adsorption is followed by the detection of the analyte which is based on the detection of the labeled binding partner, it is possible to use in accordance with the invention all those labels that have been described for immunoassays. They include, for example, enzyme labels, fluorescence dye labels, radioactive labels, labels with gold, molecules capable of generating luminescence or selenium dioxide or labels with dyed polymers, such as latex particles.

In accordance with the invention, however, it is preferred to use an enzyme as a label which is then detected in an enzymatic color reaction. Particularly preferred enzymes include β-D-galactosidase, alkaline phosphatase, or peroxidase. They can be detected by using such substrates as chlorophenolred-β-D-galactoside, p-nitrophenyl-phosphate, AMPPD (disodium-3-(methoxyspiro{1,2-dioxetane-3,2'-tricyclo[3.3.1.1.3,7]decane}phenylphosphate) or ABTS™. In another preferred embodiment of the invention, a fluorescence dye is used as a label where the fluorescence quantum yield or the depolarization capacity changes due to the binding to the antibody in dependency upon the concentration of the analyte contained in the sample liquid. When enzyme labels are used, it is particularly preferred to increase the sensitivity during the detection of the label by using an amplification system with an amplification reaction as described, for example, in DD222896, DD222897, and DD280790.

Particularly preferred labels are those which allow detection of luminescence, e.g. enzyme labels of alkaline phosphatase combined with, for example, AMPPD (disodium-3-(methoxyspiro{1,2-dioxetane-3,2'-tricyclo[3.3.1.1.3,7] decane}phenylphosphate), or CSBD (disodium 3-(methoxyspiro{1,2-dioxetane-3-2'-(5-chloro)-tricyclo [3.3.1.1.3,7]decane}phenylphosphate or peroxidase with luminol; when molecules capable of luminescence are used, aequorin (Biochemistry 1992, Vol. 31, page 1433–1442) where luminescence is triggered by calcium ions; or acridinium ester, where luminescence is triggered by peroxide.

The antibodies used in accordance with the invention are manufactured according to known methods of immunizing suitable animals with the corresponding immunogen. The antibodies are obtained after immunization and those antibodies are selected which exhibit the highest possible specificity and affinity for the analyte. The expert is also familiar with the manufacture of monoclonal antibodies and antibody fragments.

The determination is carried out such that the complex of analyte and first binding partner as well as free first binding partner from the first matrix are eluted in a first step. In this eluate, the analyte can be determined with all known immunoassays.

In a preferred embodiment, the carrier essentially comprises four zones (FIG. 1):

1. a first carrier matrix (immune adsorber) containing first binding partner (conjugate of antibody and labels) which is not bound to the carrier, 2. a second carrier matrix (capture matrix), in which the non-analyte-bound conjugate is bound to immobilized analyte analogs, and is optionally determined.

3. a third carrier matrix (detection field), in which the label is preferably determined.

4. optionally, the storage container holding liquid suitable for the elution can be disposed before the first carrier matrix. In a preferred manner, this is a carrier fleece.

To implement the determination, a pressure difference is created to draw or pump the gas to be analyzed into the first carrier matrix. After sufficient enrichment of the analyte on the immune adsorber, and a possible formation of a complex between analyte and binding partner, the elution liquid is transferred from the storage container into the first carrier matrix, for example by applying pressure: In this first step, it is also possible to have a complex formation between analyte and binding partner. The soluble components of the first carrier matrix elute in the second carrier matrix (capture matrix), where the amount of receptor which has not entered an immunological binding with the analyte is bound to excess, carrier-bound analyte analog. The conjugate of analyte and specific receptor continue to travel to the third carrier matrix in which the label is detected.

If, for example, the conjugate of antibody and acridinium ester is used on the first carrier matrix (immune adsorber), detection in the detection field is achieved by measuring luminescence triggered by alkaline peroxide. If the conjugate of an antibody and alkaline phosphatase is used on the first carrier matrix, luminescence is measured after diffusion into the second carrier matrix (capture matrix) using a luminogenic AP substrate such as Lumiphos (disodium 3-(methoxyspiro{1,2-dioxetane-3-2'-tricyclo[3.3.1.1.3,7]decane}phenylphosphate or a chromogenic AP substrate (X-Gal, NBT) in the detection field. If a conjugate of antibody and gold sol is used as conjugate, detection is carried out visually in the third carrier matrix following a chromatography via a capture matrix. Such capture matrices are described, for example, in EP-A 0052769, EP-A 0167171 and EP-A 0470565.

If the conjugate used is one of an antibody and aequorin, luminescence is measured in the third carrier matrix by means of calcium ions used to impregnate third carrier matrix or by adding calcium ions.

In another embodiment, the first binding partner (antibody) is not labelled and the mixture of analyte-antibody-complex and free antibodies which was eluted from the first matrix is incubated with a second solid phase coated with analyte analogs. Subsequently second labelled antibodies to the first analyte antibodies (preferably to the constant part thereof) are used to incubate and wash the whole mixture and to detect the amount of bound or free first antibodies eluted from the first matrix in a substrate reaction, e.g. with ABTS™. If a conjugate of analyte antibodies and label (e.g. peroxidase) is used instead of the unlabelled first analyte antibody, the incubation and washing step with the secondary detection conjugate of peroxidase and antibody to the analyte antibody can be omitted. Further, it is also possible to use an analyte antibody-acridiniumester-conjugate instead of an analyte antibody enzyme conjugate and to carry out a luminometric detection by reacting it with alkaline peroxide solution.

The conjugates of antibody and labels can be applied on the carrier materials in a simple wetting procedure. It is also possible to apply conjugate solution on the dried carrier, to allow the solution to be adsorbed and to separate excess liquid by letting it drop, by centrifuging it or rapidly aspirating air. In a preferred manner, the conjugate is applied on the carrier in a buffered solution, such as PBS, or other conventional buffers with a pH of 5–9. To improve the permeability of the carrier and to improve its stability, the solution may also contain non-denaturing detergents, such as Tween 20, Tween 80, octylglucoside, polydocanol, Synperonic F 68, or organic solvents, such as glycerol DMSO, and/or polyethyleneglycol and/or protein additives, such as bovine serum albumin or nonspecific IgG.

For the elution, it is advantageous to use buffered solution such as PBS or other conventional buffers in the pH range between 5 and 9.

Another subject matter of the invention is a device for obtaining and/or detecting an immunologically active substance in a gas phase, said device comprising
  a) a gas- and liquid-permeable carrier matrix containing a first binding partner of the analyte in an elutable form,
  b) a capture system for such an eluate in which the complex of analyte and first binding partner, or non-bound first binding partner is isolated, and, if necessary, determined in a subsequent reaction.

The matrix of the immune adsorber in accordance with the invention can be planar, such as a fleece or a membrane, or have the form of laminar layers (e.g. in the form of columns). In case of planar matrices, it is possible to use round or otherwise shaped surfaces with an area between 2 mm$^2$ and 100 cm$^2$ and a depth between 0.1 mm and 10 mm when volume currents of 1 ml to 100 l/min, preferably 100 ml to 20 l/min, particularly preferred 500 ml/min to 10 l/min are used for the adsorption. It is particularly preferred to use matrices with a surface area between 0.2 and 5 cm$^2$ and 0.5 to 2 mm in depth. If deeper layers are used, it is preferred to use column-like geometries having an area between 3 mm$^2$ and 25 cm$^2$ and layer thicknesses between 3 mm and 20 cm. A preferred area is one between 10 mm$^2$ and 100 mm$^2$ and 1 to 10 cm layer depth. The form of the matrix material can also be a sphere or a fiber; it can have irregular kernels or be a gel.

The capture system can also be planar (carrier matrix), column-like or configured as a container to hold liquid.

The carriers are preferably made of several essentially adjacent capillary active test fields (carrier matrices) which are in fluid contact with each other, so as to form a line of transportation along which liquid is propelled by means of capillary forces and through the immune adsorber toward a detection field. The number of test fields per se is irrelevant and depends whether the reagents necessary for the immunological reaction are separately applied to the fields or together.

As described in EP-A 0 374 684, a glueing agent is used to attach the test fields on a carrier foil. To allow gas to traverse, the carrier foil is provided with holes such that the test field (first carrier matrix) comes to lie above the openings. The glued carrier foil is then cut into individual carriers where the gas penetration openings are essentially in the center below the first carrier matrix.

FIGS. 1a) and 1b), wherein
  1) is a fleece for receiving elution liquid,
  2) is an immune-adsorbing matrix above an adsorption opening (3) of the carrier foil (6),
  3) is an adsorption opening
  4) is a capture matrix
  5) is a detection matrix
show an example of a test carrier.

In another embodiment, the device also contains at least one buffer field, which is in contact with immune adsorber, capture matrix, and/or detection field. It contains auxiliary substances to adjust the conditions for an optimal reaction (e.g. ion strength, pH value). The buffer field consists of a porous material, preferably a fleece made of cellulose, polyester, or nylon. Suitable carrier materials and methods for applying the conjugate are described in EP-A 0353570. Particularly suitable materials are porous materials on polyester, cellulose, or glass fiber basis.

The analyte analog can be immobilized in the capture matrix according to known methods, for example, chemically or by immune precipitation. In a preferred manner, however, a biological binding partner such as (strept)avidine is bound to the material of the capture field and the antibody, and/or the peptide in accordance with the invention is added while bound to another biological binding partner, for example biotin. Immobilization of the analyte analog or the antibody is then achieved by binding the biological binding partner (e.g. biotin/streptavidin binding). Such methods of immobilization are described in EP-A 0374684.

If necessary, the detection zone can preferably be provided with a capture matrix above or below it (cf. EP-A 0353500). The detection zone preferably contains a reagent system with a detection substrate suitable for the label which is subject to an observable change upon contact with the labeled component or it serves for direct detection of the conjugate, if a label is used which can be directly determined (e.g. fluorescence label). If it contains a substrate, this zone is preferably made of a dissolvable film or a tissue or a fleece which is hydrophobically blocked. Such carriers are described in EP-A 0353501. When it reaches the end of the field of the substrate, a sample liquid is thus eluted from the carrier and the detection reaction is triggered.

Examples for detectable substances include as drug molecules cocaine, heroin, cannabinol, cannabidiol, tetrahydrocannabinol; examples for explosives include nitroglycol, nitroglycerin, nitropenta, hexogen, octogen, tetranitromethane, trinitrotoluene, trinitrobenzene, trinitroanisol, triaminotrinitrotoluene, hexanitrostilben, and polycyclic aromatic hydrocarbons, polychlorated biphenyls, herbicides, and pesticides (such as atracin, parathion, simacin) and odoriferous compounds (e.g. terpineol, limes, caryophylls, camphor, farnesol).

Figure 2:
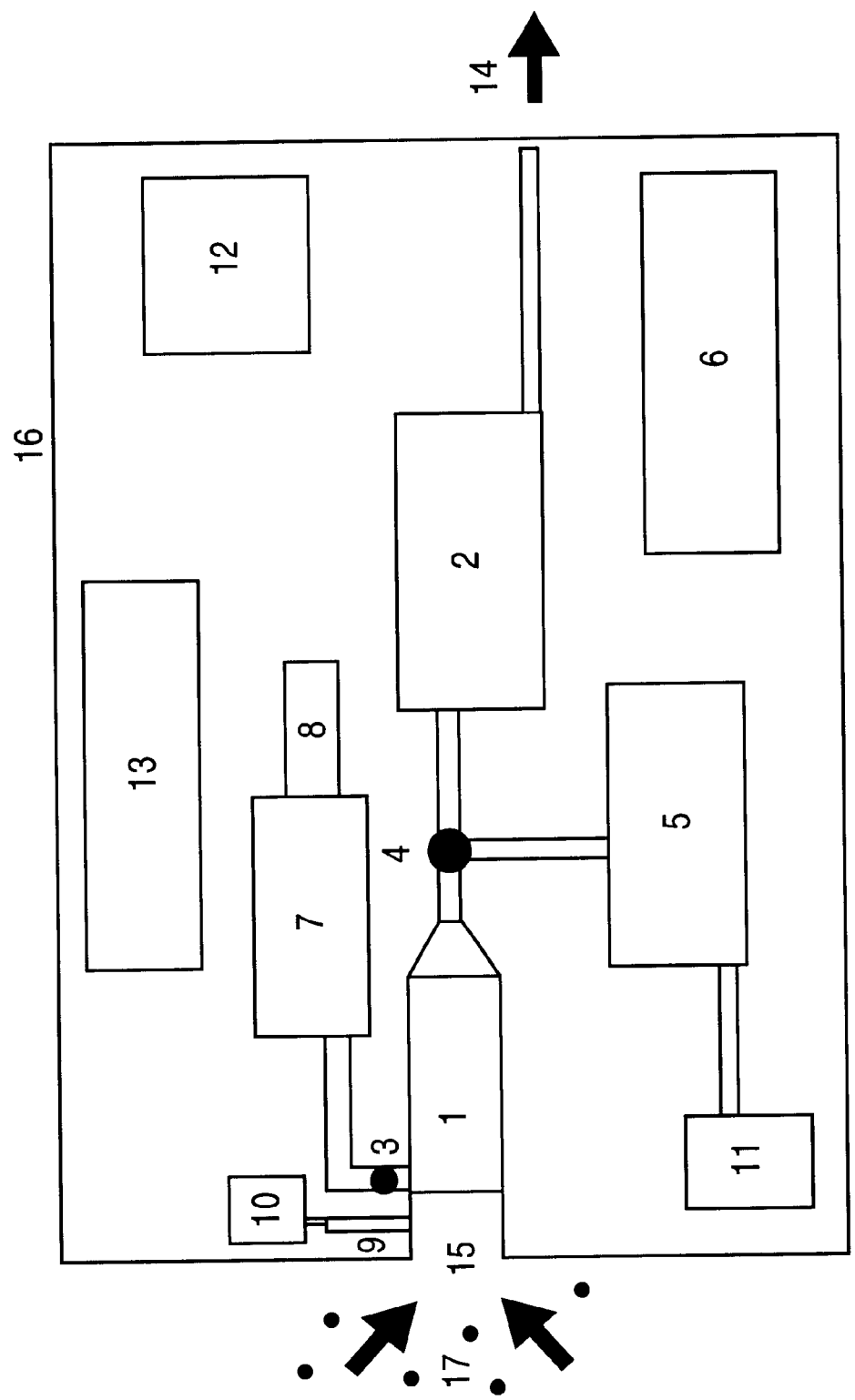
FIG. 2 shows a device in which a vacuum pump draws a sample gas across an immune adsorber and the gas is exhausted through an outlet. During this process the valve between the immune absorber and the detection unit is closed. After the sample is drawn across the immune absorber, the valve between the immune absorber and the vacuum pump is closed while the valve between the immune absorber and the detection unit is opened. Eluting liquid then flows through the immune absorber and through the detection unit. The amount of analyte can be determined in the detection unit in a subsequent immunological reaction.

A preferred embodiment (FIG. 2) of the device comprises the following elements:

1. immune adsorber in accordance with the invention
2. vacuum pump
3. valve
4. three-way valve
5. detection unit
6. signal processing and display
7. storage device with eluting agent
8. pressure pump
9. glider
10. drive unit for glider
11. recess for measuring solution
12. power supply
13. operating console
14. gas outlet
15. sample gas inlet
16. housing
17. gas-like sample molecules, sample molecules bound to particles, or particle-like sample.

In a first working cycle, a vacuum pump 2 is used to draw in sample gas containing molecules 17 to be adsorbed through sample inlet 15 across immune adsorber 1.

The gas will be exhausted by the device through outlet 14. If necessary, sample particles which adhere to the material to be analyzed or particles to which sample molecules are adsorbed are brought into the intake current by means of blowing or brushing. To accomplish this, valve 3 is closed, valve 4 between immune adsorber and vacuum pump is open, and glider 9 is opened prior to sample intake. Once the adsorber 1 is charged with the amount of sample gas to be analyzed, drive 10 is activated to close glider 9.

Subsequently, valve 3 is opened and at the same time valve 4 is switched to allow free passage between adsorber and detection unit. Pressure pump 8 is now used to transport eluting agent from the storage container 7 through the immune adsorber. The eluting liquid which, at the outlet from adsorber 1, now contains the conjugate of analyte molecule 17 and the labeled antibody, and, depending on the amount of analyte contained in the sample gas, also unbound labeled antibody, is now made available to another unit. This is a detection unit 5 in which the amount of analyte molecules 17 present in the sample is determined in a subsequent (immunological) reaction. Then, pressure pump 8 is again activated to transport eluting agent from storage container 7 through the system. The system is thus washed and at the same time used measuring solution is transported to a receptacle 11. The signals contained in the detection unit are processed and displayed by means of a function unit 6 which is operated via operating field 13. Power supply to all components is effected via an exchangeable storage battery 12 and all components are disposed in a housing 16.

The antibody antigen complex from the first carrier matrix is transferred to the other carrier matrices and/or reaction vessels preferably by mechanically squeezing the solvent which is present in the first carrier matrix, by applying and pressing through an additional eluting agent via pressure or aspiration. Instead of using mechanical pressure, the transport of additional eluting agent can also be continued by means of capillary forces/concentration gradients/hydrostatic pressure.

It is preferred to remove the solvent by means of squeezing or to pass through additional eluting agents by pressing or drawing which requires pressure or the application of a vacuum.

EXAMPLE 1 a) Preparation of Benzoylecgonine Maleimidoethylamide

In 200 ml of dried acetonitrile, 1 g N-hydroxysuccinimide and 1.8 g dicyclohexylcarbodiimide are added to 2.4 g benzoylecgonine hydrochloride, which is then stirred for 3 hours. The precipitate is removed by filtration, the filtrate is evaporated, taken up in nitromethane and again filtered. After evaporating the solvent, it is triturated with ether. The result is 1.13 g of benzoylecgonine succinimidylester. Together with 0.47 g maleimidoethylamine hydrochloride (cf WO 90/15798), this product is taken up in 100 ml dried acetonitrile. 1.1 g of triethylamine are added and stirred for 12 hours at room temperature. The reaction mixture is evaporated, taken up in 50 ml ethylacetate and extracted 3 times with sodium hydrogen carbonate solution. The ethyl acetate phase is evaporated and the product is converted into the hydrochloride by taking it up in 10 ml of dioxane saturated with HCl. The result is again filtered, washed with ether and produces 1 g of benzoylecgonine maleimidoethylamide hydrochloride.

b) Preparing the Cocaine Immunogen

Contained in 25 ml of 0.1 mol potassium phosphate buffer at pH 8.5, 300 mg of bovine serum albumin are reacted with 106.6 mg of S-acetylthiopropionic acid succinimidylester, dissolved in 5 ml of dioxane, over a period of 3 hours at room temperature. The modified bovine serum albumin is separated from low-molecular reaction products in a gel chromatography over ACA 202 using 0.1 mol potassium phosphate buffer, pH 8.5. The result is a solution of 310.5 mg of product in 57.5 ml potassium phosphate buffer, pH 8.5.

An amount of solution which corresponds to 100 mg of the modified bovine serum albumin is reacted with 4.7 ml of a 1 M hydroxylamine solution. Subsequently, 49.4 mg benzoylecgonine maleimidoethylamidehydrochloride are added and allowed to react for 12 hours at 4° C. The resulting cocaine immunogen is separated from the low-molecular reaction products in a gel chromatography over ACA 202 using 0.1 mol potassium phosphate buffer, pH 8.5. The results are 95 mg of cocaine immunogen dissolved in 0.1 molar potassium phosphate buffer, pH 8.5.

c) Obtaining Antibodies to Cocaine 10 sheep were immunized with the cocaine immunogen in a complete Freund's adjuvans. The dose administered to each animal was 200 μg for the first and for each following immunization. Immunization were carried out in monthly intervals. The resulting sera were assayed in a microtiter plate assay for the presence of antibodies to cocaine. To do this, streptavidin-coated microtiter plates were incubated with benzoylecgonine-[N'-biotinylaminocaproyl-(3,6-dioxa-8-aminooctyl)amide], prepared from benzoylecgonine succinimidylester and N-(biotinylaminocaproyl)-1,8-diamino-3,6-dioxaoctane, washed, then again incubatred with a sera to be analyzed, washed and, for the purpose of detection, incubated with a conjugate of peroxidase and a rabbit-anti-sheep-immunoglobulin, washed and a substrate was added. The relative affinities to cocaine were determined corresponding to example 12 of EP-A 0547 029. Sera from S 4987 with a good affinity to cocaine were selected for additional tests.

d) Preparing Conjugates of Antibodies to Cocaine and Alkaline Phosphatase

Polyclonal sheep antibodies to cocaine, DE-purified (PAB<cocaine>S-IgG(DE)) are isolated from delipidized raw serum (sheep) according to methods which are known to the expert using ammonia sulfate precipitation and DEAE-sepharose chromatography.

Immuneresorptive Purification of PAB<BZE>S-IgG(DE)
Preparing of a Cocaine Immune Adsorber The cocaine polyhapten of example 1b (without biotinylation step) is bound to a glutardialdehyde-activated affinity adsorbens (activated Spherosil, Boehringer Mannheim, Cat. -No. 665 525) in accordance with the specifications of the manufacturer.

Immunesorption

The (PAB<cocaine>S-IgG(DE)) is dialyzed against PBS/azide (50 mmol/l potassium phosphate, pH 7.5, 150 mmol/l sodium chloride, 0.1% sodium azide) and then added over a suitably dimensioned adsorption column (depending on the binding capacity of the adsorption and the titer of the IgG(DE)) over a period of 2 h at room temperature. After washing nonbound protein with PBS/azide, the bound antibody is eluted with 1 M propionic acid at room temperature.

The eluate is dialyzed against 30 mM sodium phosphate buffer, pH 7.1.

Preparation of PAB<BZE>S-IgG(IS)-AP Conjugates
Activating the IgG

The immunosorptively purified IgG is incubated at a concentration of 10 mg of protein/ml in 30 mM sodium phosphate buffer, pH 7.1, with a 5-fold molar excess of maleimido-hexanoyl-N-hydroxy-succinimide ester (MHS) at 25° C. over a period of 1 hour. The mixture is stopped by adding 100-fold molar excess of L-lysine/HCl as compared to MHS and dialyzed against 10 mM potassium phosphate, 50 mM sodium chloride, 10 mM MgCl$_2$, pH 6.1.

Activating Alkaline Phosphatase

The alkaline phosphatase (EIA quality, Boehringer Mannheim, Cat. No. 567 744) is, at a concentration of 10 mg of protein/ml in 30 mM triethanolamine, 3 M NaCl, 0.1 mM ZnCl$_2$, 1 mM MgCl$_2$, pH 7.0, incubated for 1 hour at 25° C. with a 30-fold molar excess of succinimidyl acetylthiopropionate (SATP). The reaction mixture is stopped at 10 mM by adding L-lysine/HCl and dialyzed against 10 mM potassium phosphate, 50 mM NaCl, pH 7.5. 1 M hydroxylamine solution, pH 7.5, at 20 mM and 0.1 M EDTA solution up to 0.5 mM are added to deacetylate the protected SH group and the mixture is incubated for 15 min at 25° C. The activated AP solution is immediately used for the coupling.

Coupling

The solutions of the activated AP and the activated IgG are mixed in equimolar amounts, and the pH is adjusted to 6.8–7.0, and the AP concentration is adjusted to 5 mg/ml using redistilled water. After 3 hours of reaction at 25° C., the mixture is stopped by sequentially adding N-ethylmaleimide (up to 5 mM, 30 min 25° C.) and 1 M hydroxylamine solution, pH 7.5 (at 20 mM, 1 h, 25° C.). The conjugate solution is dialyzed against 50 mM triethanolamine/HCl, 150 mM NaCl, 1 mM MgCl$_2$, 0.1 mM ZnCl$_2$, pH 7.6, and spiked up to 10 mg/ml bovine serum albumin and 3 M NaCl.

e) Preparing a Biotinylated Cocaine Polyhapten

At a concentration of 25 mg/ml in phosphate buffer, pH 8, rabbit IgG is reacted with the 6-fold molar amount of S-acetylthiopropionic acid succinimidyl ester, dissolved in dimethylsulfoxide. After 1 h at 25° C., the reaction is stopped by adding a solution of 1 mol/l lysine. Then a dialysis is carried out against 0.1 mol/l potassium phosphate buffer, pH 6 using 1 mmol/l EDTA. Subsequently, the pH is adjusted to 7.8 and incubated with 1 mol/l hydroxylamine solution, pH 7.5 at 20 mmol/l for 1 h at 25° C. To accomplish the coupling, a 5-fold molar excess of benzoylecgonine maleimidoethylamidehydrochloride, dissolved in dimethylsulfoxide, and is under stirring added to the solution of the rabbit IgG which is modified with sulfhydryl groups. After incubating for 2 hours at 25° C., the reaction is stopped by successively adding 0.1 mol/l cystein solution up to 1 mmol/l and 0.5 mol/l iodine acetamide solution up to 5 mmol/l. The mixture is dialyzed overnight against 0.1 mol/l potassium phosphate buffer, pH 8.5, and via membrane filtration concentrated to a protein concentration of 10 mg/ml. Then, the resulting cocaine polyhapten is biotinylated with an 8-fold molar excess of biotinylcaproic acid succinimidyl ester, dissolved in dimethylsulfoxide. The mixture is dialyzed against 20 mmol/l sodium acetate, pH 4.3, and purified via FPLC.

EXAMPLE 2 a) Preparing a First Carrier Matrix (Immune Adsorber) with a Conjugate Consisting of Anti-cocaine Antibody and Alkaline Phosphatase A fleece was prepared which consists of 80 parts polyester fibers with a linear density of 3.3 dtex and a length of 4 mm, 20 parts viscose staple fiber with a linear density of 1.7 dtex and a length of 3 mm, and 20 parts polyvinyl alcohol fibers with a length of 4 mm. The fiber materials polyester, viscose staple fiber and polyvinyl alcohol were broken open/separated in mixing tubs at a density of 0.3% using fully deionized water. The fiber material was then pumped to a circulating sieve. While water was removed from the fiber mixture, i.e. drawn off by producing a vacuum, fibers oriented themselves on the sieve side and were contact-dried as a fleece with a drying contents of approximately 20% over drying cylinder. The result is a fleece with an area weight of 80 g/cm$^2$ and a thickness of 0.32 mm.

On the fleece, circular disks with a diameter of 18 mm were punched out and each was impregnated with 20 μl of a solution of the concentration 500 ng/ml of the conjugate of anti-cocaine antibody and alkaline phosphatase (free first binding partner) which was prepared according to example 1d. The result is an embodiment of the immune adsorber in accordance with the invention.

b) Measuring Cocaine from the Gas Phase

Figure 3:
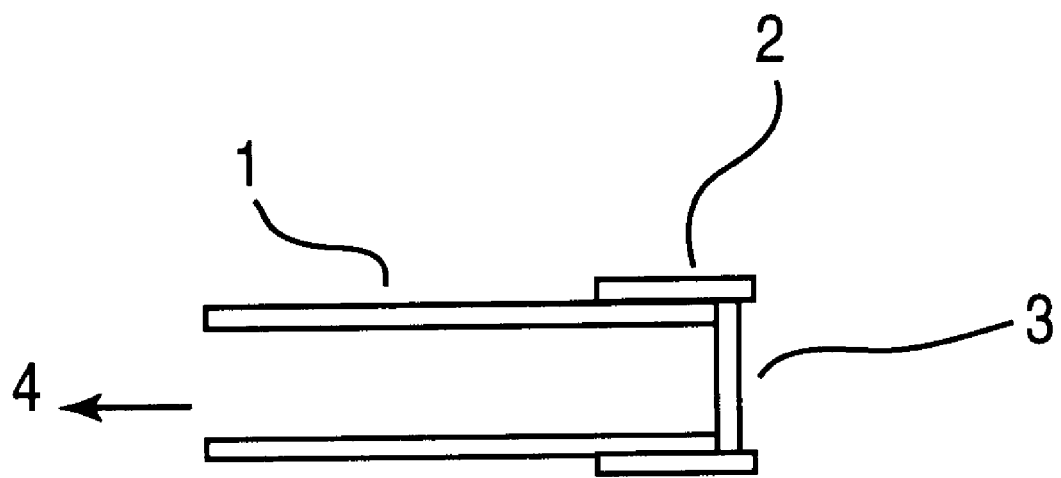
FIG. 3 shows an embodiment where the immune adsorber is on a support connected to a flow through controlled vacuum pump.

The immune adsorbers in accordance with the invention are placed into a support according to FIG. 3 The support with the immune adsorber mounted thereto is connected to a flow-through controlled vacuum pump (type GSA 50-01). In the drawing, the reference numerals mean the following:

1) plastic tube 2) guide for fleece-like adsorber material 3) fleece-like adsorber material 4) suction direction toward the vacuum pump The cocaine gas phase is provided by means of a test stand where nitrogen gas is passed through an also heated up base body of solid cocaine (free base) at 20° C. The entire gas conduct of the test stand is carried out under isothermal conditions to ensure uniform gas quality. The presence of a constant gas quality at the output of the test stand is determined with a reference analysis instrument (introducing the test gas in several consecutively disposed condensation trap, analysis with GC/MS). At a given temperature of 20° C., a cocaine concentration of approximately 2 ng/l is maintained which corresponds to the saturation of concentration of cocaine to be theoretically expected for this temperature (Lawrence et al., Can. J. Chem. 62, 1984). In an additional dilution segment, the cocaine gas is diluted with nitrogen to produce 1% of the saturation concentration, i.e. 20 pg/l or $6.6 \times 10^{-14}$ mol/l of cocaine.

At the support, a through-put of 5 l/min is set which is checked with a flow meter (rotameter) disposed in the gas conduit. Here, a pressure decrease of approximately 140 mbar is observed. With the given flow rate, diluted cocaine gas is applied to the adsorber material at the output of the test stand for 30 sec, 1 min, 2 min, 4 min, and 8 min. This corresponds to total amounts of 50, 100, 200, 400, and 1000 ng of cocaine with which the immune adsorber comes into contact.

The immune adsorbers are then shaken with 400 µl of elution buffer (50 mmol HEPES, 0.9% NaCl, 0.05% Tween 20, pH 6.8) for a period of 1 min.

The wells of a microtiter plate are then incubated with 100 µl of a solution of 10 ng benzoylecgonine-[N'-biotinylaminocaproyl-(3,6-dioxa-8-aminooctyl)amide] in elution buffer for 60 min and then washed 3 times with washing buffer (0.9% NaCl+0.05% Tween 20).

Portions of 100 µl of the immune adsorber eluate, which contains free first binding partner (conjugate of anti-cocaine antibody and alkaline phosphatase) and complex of free first binding partner and cocaine, depending on the amount of adsorbed cocaine, are added into the wells of the microtiter plate, incubated for 60 min and then washed 3 times with washing buffer.

To carry out the detection reaction, 100 µl of substrate solution (0.4 mmol/l CSBD disodium 3-(methoxyspiro{1,2-dioxetane-(5-chloro)-3,2'-tricyclo[3.3.1.1.$^{3,7}$] decane}phenylphosphate, 10% Sapphire enhancer in 0.1 M diethanolamine, 1 mmol/l $MgCl_2$, pH 10.0) were added and luminescence was measured for 60 sec.

Measurement results

| Amount of cocaine applied [pg] | Luminescence [rel. units/60 sec] |
| --- | --- |
| 0 | 6767.2 |
| 50 | 5602.3 |
| 100 | 4766.8 |
| 200 | 3901.7 |
| 400 | 3834.3 |
| 800 | 3871.0 |

Figure 4:
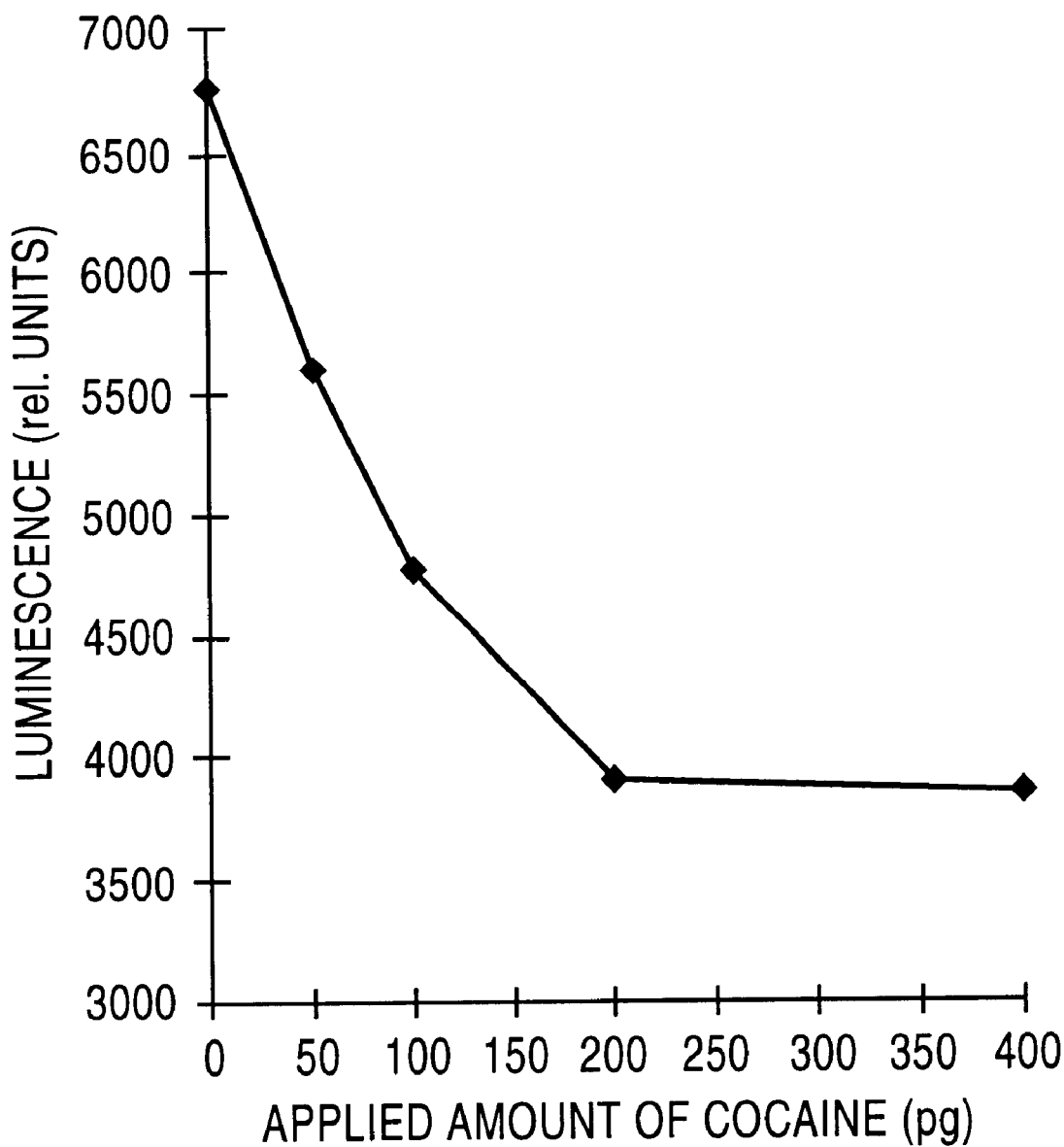
FIG. 4 shows a calibration curve obtained by plotting the amount of cocaine applied and the luminescence measured according to example 2.

The resulting calibration curve is shown in FIG. 4.

In a comparative test, using an exactly weighed amount of cocaine in the immunoassay, the yield of cocaine measured after adsorption and elution referred to cocaine applied amounted to 79%.

EXAMPLE 3

Figure 1B:
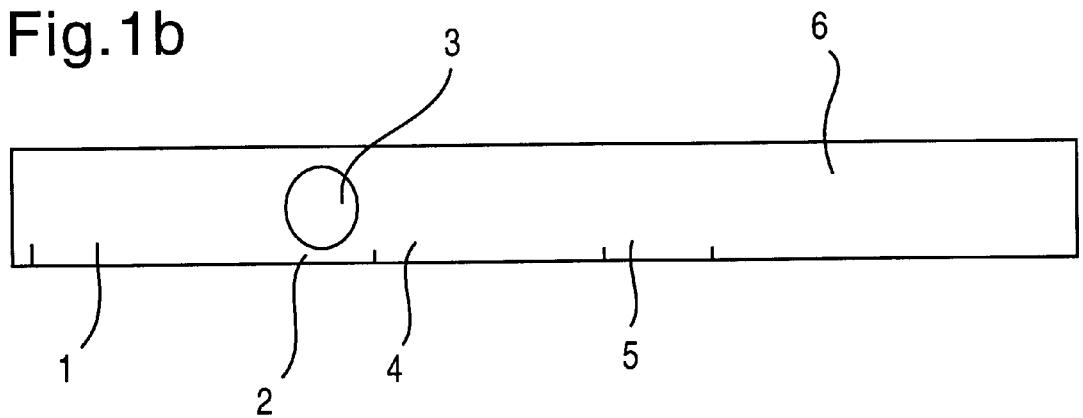

Structure of Carrier (FIG. 1)

Carrier Fleece (1)

The polyester fleece was manufactured by Binzer, Hatzfeld, Federal Republic of Germany. It is a pure polyester fleece, reinforced with 10% kuralon. The thickness 1.0–1.2 mm, the suction capacity amounts to 1800 ml/m$^2$.

First Carrier Matrix (Immune Adsorber) (2)

A mixed fleece consisting of 80 parts polyester and 20 parts viscose staple fiber, reinforced with 20 parts of kuralon, with a thickness of 0.32 mm and an adsorption capacity of 500 ml/m$^2$ is impregnated with the following solution and then dried: $3.8 \times 10^{-8}$ mol/l of conjugate consisting of anti-cocaine antibody and alkaline phosphatase (free first binding partner), which was manufactured according to example 1d and 3 mmol/l NaCl, 1 mmol/l $MgCl_2$, 0.1 mmol/l $ZnCl_2$, 30 mmol/l triethylamine, pH 7.6.

Second Carrier Matrix (Capture Matrix) (4)

A fleece consisting of 100% linters, reinforced with 20% etadurin having a thickness of 0.35 mm and an adsorption capacity of 372 ml/m$^2$ is impregnated with the following solution and then dried: 10 mmol/l sodium phosphate, pH 7.5, polymerized streptavidin 200 mg/l (manufactured according to example 1c, EPS 0 331 127).

The preimpregnated fleece is then again impregnated and then dried: 10 mmol/l sodium phosphate, pH 7.5, 200 mg/l biotinylated,cocaine polyhapten according to example 1c.

Third Carrier Matrix (Detection Field) (5)

A fleece made of 100% linters, reinforced with 2% etadurin and a thickness of 0.35 mm and a suction capacity of 372 ml/m$^2$ is used.

Carrier matrices were glued onto a carrier foil of 6 mm in width as shown in FIG. 1. The carrier foil has an aspiration opening (3) of 3 mm in diameter, which is disposed in the center below the first carrier matrix (immune adsorber).

b) Measuring Cocaine from the Gas Phase

The carriers were placed into a support featuring a guide for a tube with an O-ring to seal it. As described in example 2b, the tube is connected to a vacuum pump. While the gas sample is collected, the tube with the O-ring below the first carrier matrix is pressed against the carrier foil such that the sample gas flows through the first carrier matrix and the opening in the carrier foil.

Cocaine gas with a saturation of 0.1%, i.e. 2 pg/l or $6.6 \times 10^{-15}$ mol/l of cocaine (manufactured according to example 2b) is aspirated across the first carrier matrix (immune adsorber) of the carrier at a flow rate of 2 l/min for a period of 15 sec (total amount: 1 pg) and for 2.5 min (total amount: 10 pg).

Cocaine gas with a saturation of 10%, i.e. 200 pg/l or 6.6×10$^{-13}$ mol/l of cocaine (manufactured according to example 2b) is aspirated across the first carrier matrix (immune adsorber) of the carrier at a flow rate of 1 /min for a period of 30 sec (total amount: 100 pg) and at a flow rate of 10 l/min for 30 sec (total amount: 1000 pg).

Then, the carrier is removed from the support and the carrier fleece is immersed in the buffer solution (150 mmol/l NaCl, 50 mmol/l potassium phosphate buffer, pH 7.2) for a period of 10 sec. The liquid taken up by the carrier fleece chromatographs to the third carrier matrix (detection field). Using a DIN 821 puncher, a circular part is punched out of the third carrier matrix and placed into a well of a microtiter plate with the top of the fleece facing up. In a luminescence microtiter plate reader (Luminoscan), 100 μl of substrate solution (Lumiphos 530, preparation of disodium 3-(methoxyspiro{1,2-dioxetane-3,2'-tricyclo[3.3.1.1.$^{3,7}$] decane}phenylphosphate, Boehringer Mannheim) are added. The luminescence is measured over a period of 10 min.

In order to determine the blank value, the carriers are immersed into buffer solution, allowed to chromatograph and analyzed without cocaine gas being aspirated Measurement results

| Amount of cocaine applied [pg] | Luminescence [rel. units/60 sec] |
|---|---|
| Blank | 60.46 |
| 1 | 76.86 |
| 10 | 106 |
| 100 | 134.4 |
| 1000 | 244.7 |

Figure 5:
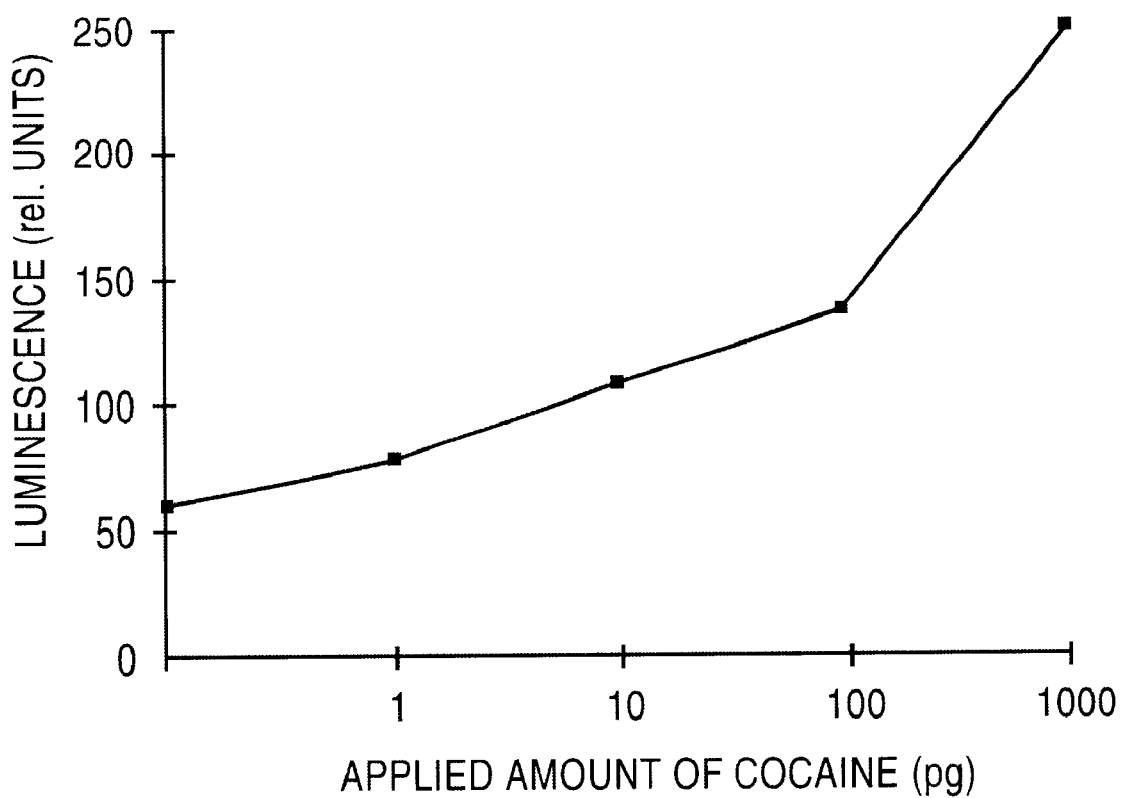
FIG. 5 shows a calibration curve obtained by plotting the amount of cocaine applied and the luminescence measured according to example 3.

The resulting calibration curve is shown in FIG. 5.

EXAMPLE 4

Instead of the cocaine gas used in the test stand described in connection with example 2b, a gas containing cocaine particles is aspirated onto the first matrix (immune adsorber) from example 2a and/or the carrier of example 3. Samples were taken at 1 cm above a polyethylene surface which had previously been contaminated with a powder-like mixture of 1 part of cocaine and 1000 parts of lactose. 5 mg of this mixture were spread over surface area of 220 cm$^2$. While the samples were taken, the surface was also exposed to a pressurized air current of 5 l/min generated by a nozzle with approximately 1 mm in diameter from a distance of approximately 1 cm in order to support the removal of particle-like contamination. All tests produced measurements corresponding to a cocaine amount of smaller than 1 ng.

What is claimed is:

1. A device for obtaining an analyte contained in a gas phase, comprising
   a) a gas- and liquid-permeable carrier matrix containing a first binding partner of an analyte in elutable form,
   b) a capture matrix which binds a complex consisting of said analyte and said first binding partner or a noncomplexed first binding partner, wherein an analyte analogue or antibody specific for the complex of said analyte and said first binding partner is immobilized on said capture matrix, and
   c) a means for drawing a sample gas across said gas- and liquid-permeable carrier matrix containing a first binding partner of an analyte in elutable form, wherein said means does not draw said gas through said capture matrix.

2. The device according to claim 1, further comprising an eluting liquid which elutes the analyte from the carrier matrix.

3. The device according to claim 1, wherein said gas- and liquid-permeable carrier matrix has a gas permeability between 10 ml/min to 10 l/min.

4. The device according to claim 1, wherein said gas- and liquid-permeable carrier matrix is in a planar form or in the form of laminar layers.

5. The device according to claim 1, wherein said first binding partner is detectably labelled.

6. The device according to claim 1, wherein said means for drawing a sample gas containing an analyte through said gas- and liquid-permeable carrier matrix is a vacuum pump.

* * * * *

UNITED STATES PATENT AND TRADEMARK OFFICE
CERTIFICATE OF CORRECTION

PATENT NO. : 6,605,444 B1
DATED : August 12, 2003
INVENTOR(S) : Christian Klein et al.

It is certified that error appears in the above-identified patent and that said Letters Patent is hereby corrected as shown below:

<u>Title page,</u>
Item [73], Assignees, please delete "Deutsche Aerospace AG, Munich (DE)".

Signed and Sealed this

Twentieth Day of April, 2004

JON W. DUDAS
*Acting Director of the United States Patent and Trademark Office*